United States Patent [19]

Fellegara et al.

[11] Patent Number: 5,592,374
[45] Date of Patent: Jan. 7, 1997

[54] PATIENT IDENTIFICATION AND X-RAY EXAM DATA COLLECTION BAR CODE SYSTEM

[75] Inventors: Peter C. Fellegara, Fairport; Robert W. Apps, Rochester; Mervet E. Heartberg, Webster; Richard E. Osiecki, Hemlock, all of N.Y.

[73] Assignee: Eastman Kodak Company, Rochester, N.Y.

[21] Appl. No.: 86,967

[22] Filed: Jul. 2, 1993

[51] Int. Cl.⁶ .................................................. G06F 159/00
[52] U.S. Cl. ........................ 395/203; 128/653.1; 378/204; 235/375; 395/228
[58] Field of Search ......................... 364/413.01, 413.02, 364/413.13; 235/462, 470, 472, 375; 128/653.1; 378/204

[56] References Cited

U.S. PATENT DOCUMENTS

| | | | |
|---|---|---|---|
| 31,847 | 3/1885 | Luckey | 250/327.2 |
| 3,848,112 | 11/1974 | Weichselbaum et al. | 235/61.7 R |
| 3,872,448 | 3/1975 | Mitchell | 340/172.5 |
| 3,940,742 | 2/1976 | Hudspeth et al. | 340/172.5 |
| 4,053,951 | 10/1977 | Hudspeth et al. | 364/415 |
| 4,216,462 | 8/1980 | McGrath et al. | 340/150 |
| 4,315,309 | 2/1982 | Coli | 364/200 |
| 4,591,974 | 5/1986 | Dornbush et al. | 364/200 |
| 4,641,242 | 2/1987 | Kimura | 364/414 |
| 4,739,480 | 4/1988 | Oono et al. | 364/414 |
| 4,835,372 | 5/1989 | Gombrich et al. | 235/375 |
| 4,853,521 | 8/1989 | Claeys et al. | 235/375 |
| 4,857,713 | 8/1989 | Brown | 235/375 |
| 4,857,716 | 8/1989 | Gombrich et al. | 235/462 |
| 4,885,468 | 12/1989 | Shimura | 250/327.2 |
| 4,916,441 | 4/1990 | Gombrich | 340/712 |
| 4,991,091 | 2/1991 | Allen | 364/413.02 |
| 5,006,699 | 4/1991 | Ginkel et al. | 428/42 |
| 5,099,424 | 3/1992 | Schneiderman | 364/413.02 |
| 5,140,518 | 8/1992 | Ema | 304/413.01 |
| 5,157,603 | 10/1992 | Scheller et al. | 304/413.01 |
| 5,235,510 | 8/1993 | Yamada et al. | 304/413.02 |
| 5,291,399 | 3/1994 | Chaco | 364/413.02 |
| 5,296,688 | 3/1994 | Hamilton et al. | |

Primary Examiner—Gail O. Hayes
Assistant Examiner—Hayward A. Verdun
Attorney, Agent, or Firm—William F. Noval

[57] ABSTRACT

In storage phosphor radiography a latent x-ray image of a patient is stored in a storage phosphor. A storage phosphor reader converts the latent image into an x-ray image signal. A patient identifying and exam collection bar code system provides patient identification and x-ray exam data at the time of the exam which is matched with the x-ray image signal in the reader.

3 Claims, 10 Drawing Sheets

QC Exams

Patient Information

Patient Name
Robins, Janet E.
Patient ID
123-45-6789
Date of Birth
08-10-1965
Patient Sex
Female
Radiologist
Dr. Joanne Vane
Referring Physician
Dr. Lance Underwood
Room-Unit Number
222
Bed Number
13
Destination(s)

ICU1 PDS
ICU2 PDS
Radiology KELP

Update  Reset  Done

FIG. 7

PATIENT IDENTIFICATION AND X-RAY EXAM DATA COLLECTION BAR CODE SYSTEM

FIELD OF THE INVENTION

This invention relates in general to storage phosphor radiography in which a latent x-ray image of a patient stored in a storage phosphor is converted to an x-ray image signal. More particularly, the present invention relates to a storage phosphor radiography patient identification system for matching patient x-ray exam data with the patient's x-ray image.

BACKGROUND ART

In conventional film/screen radiography, a commonly used patient identification system has the following features.

1. A requisition is filled out by the radiologist ordering a specific exam to be performed on a patient. The requisition is sent to the radiology department.

2. A technologist takes the requisition, an x-ray film cassette, and a portable x-ray generator to the patient bedside.

3. The technologist performs the exam and the film is exposed to x-rays.

4. The requisition is taped to the cassette and the exposed film is taken to the darkroom.

5. A preprinted information card is "flashed" on to the film. Such information includes the patient name, medical record number, birth date, hospital name, current date and other standard information.

6. The film is processed, and the radiology technologist verifies that a "good" image has been recorded.

7. A sticker is applied to the film which records the date, time of exposure, technique, and technologist identification.

8. The finished x-ray film is placed on a light box for review and diagnosis by a radiologist or physician.

Because of the inherent disadvantages of film radiography in the acquisition, storage and transmission of x-ray images, there has been proposed a storage phosphor radiography system. Temporary x-ray images stored in a storage phosphor are converted into an x-ray image digital signal which can be stored, processed and transmitted. As described in U.S. Pat. No. Re. 31,847, reissued Mar. 12, 1985 to Luckey, a photostimulable phosphor sheet is exposed to an imagewise pattern of short wavelength radiation, such as x-ray radiation, to record a latent image pattern in the photostimulable phosphor sheet. The latent image is read out by stimulating the phosphor with a relatively long wavelength stimulating radiation, such as red or infrared light. Upon stimulation, the stimulable phosphor releases emitted radiation of an intermediate wavelength, such as blue or violet light, in proportion to the quantity of x-ray radiation that was received. An x-ray image signal is produced by scanning the stimulable phosphor sheet in a raster pattern by means of a beam of laser light deflected by an oscillating or rotating scanning mirror. The emitted radiation is sensed by a photodetector to produce an electrical x-ray image signal. This signal may then be stored, transmitted, or displayed on a monitor or reproduced as an x-ray film.

As with film-based radiography, storage phosphor radiography requires the matching of an x-ray image with the patient. In situations where many x-rays are taken, such as in an intensive care unit of a large hospital, the management of identification of x-rays with patients can be monumental. In order to process an x-ray image signal as a function of x-ray exposure conditions, it is also desirable to match x-ray exposure conditions and other patient identification data with the x-ray image signal. Such matching results in proper diagnosis by a diagnostician (such as a radiologist) who views the x-ray image on a monitor or x-ray film reproduction.

In a known storage phosphor radiography system, patient information is entered into a workstation and is transferred to a magnetic card. (See, for example, U.S. Pat. No. 4,641,242, issued Feb. 3, 1987, inventor Kimura; U.S. Pat. No. 4,739,480, issued Apr. 19, 1988, inventors Oona et al.; U.S. Pat. No. 4,885,468, issued Dec. 5, 1989, inventor Shimura.) After an x-ray exposure on a storage phosphor is made, a technician places the cassette containing the exposed storage phosphor into a reader and dumps the patient data into the reader by swiping the magnetic card through an associated magnetic card reader. Many problems exist with this system, including double entry of patient data, which is typically entered into a computer at the time a patient is admitted into a hospital. Moreover, the specific ordering of computed radiography cassettes and patient data must be maintained.

The health care bar code identification systems disclosed in the following patents are not entirely suitable for use in storage phosphor radiography systems: U.S. Pat. No. 4,857,713, issued Aug. 15, 1989, inventor Brown; U.S. Pat. No. 5,006,699, issued Apr. 9, 1991, inventors Felkner et al.; U.S. Pat. No. 4,835,372, issued May 30, 1989, inventors Gombrich et al.; and U.S. Pat. No. 4,857,372, issued Aug. 15, 1989, inventors Gombrich et al.

A storage phosphor radiography patient ID system using a hand-held bar code scanner has been proposed in commonly-assigned, copending U.S. patent application Ser. No. 963,036, filed Oct. 19, 1992. The disclosed system records data using a hand-held bar code scanner. Because this image will be recorded, processed, transmitted, and archived digitally by a computer, the exam data also needs to be in digital form to travel with the image. The exam data is read in directly from the bar code scanner by the storage phosphor reader into a header file which is associated with the image file. The image is quality assured by a radiology tech using an electronic view box (video monitor), and the image is printed on film with the necessary information by a laser printer. Thus, no "post-processing" is required.

There has been proposed in copending U.S. application Ser. No. 981,144, filed Nov. 24, 1992, inventors Godlewski et al., a quality control workstation linked to a storage phosphor reader. The quality control workstation provides a radiology technologist with several functions including checking images acquired from a storage phosphor reader (or other sources of digital radiographic images, correcting patient information and x-ray exam information, adjusting image parameters such as image orientation and window width and leveling, routing acceptable exams and images to designated destinations (such as, remote high resolution workstations, magnetic or optical archival image storage, radiographic laser, CRT or thermal printers). Although patient information entered at the time of an x-ray exam can be changed or supplemental at the workstation.

It is desirable that a patient identification x-ray exam collection bar code system have the following features which are not fulfilled in known ID/collection bar code systems.

1. Easier entry of patient and technologist IDs.

2. Ability to review all data that has been collected.

3. Common comments do not have to be entered in on a keypad.

4. Ability to easily delete a record.

5. Ability to have required data fields and default fields.

6. Support many common bar code standards.

There is thus a problem in providing a patient ID/x-ray exam data collection bar code system which incorporates these desirable features and obviates the disadvantages of the prior art.

SUMMARY OF THE INVENTION

According to the present invention, there is provided a patient ID/x-ray exam data collection bar code system which obviates the disadvantages of the prior art. The present invention has the following advantageous features.

1. Ability to review all of the data that has been collected.

2. Patient IDs (bar codes) have been encoded. This provides for easy entry of the patient ID. A two step entry process is now reduced to a one step operation.

3. Technologists IDs (bar codes) have been encoded. This provides for easy entry of the technologists ID. A two step entry process is now reduced to a one step operation.

4. Common comments do not have to be typed in with the key pad. Bar codes have been defined for common comments.

5. Ability to easily delete a record (file for one patient).

6. Ability to designate any of the fields as being Required fields. A technologist would then be required to enter this data before the patient record is completed. The fields that are required can be set by each customer at the customer site. A special application using a required fields bar code sheet has been developed.

7. Some of the fields may be defaulted to a predetermined value. This provides for faster data input at the patient bed side in the ICU. Fields that always have the same value for a given hospital can be defaulted to that value. For each patient, only exceptions are inputted. If no default values programming bar code sheet.

8. Support many common bar code standards to read existing bar code information in the hospital (patient ID, requisition number, etc.).

9. All bar codes on the exam data collection card are coded. This provides easy bar code printing and support for multiple languages.

According to the present invention there is provided a patient identification and x-ray exam data collection bar code system, comprising:

a patient bar code adapted to be located with a patient for identifying a patient;

a storage phosphor for storing an x-ray image of a patient, said storage phosphor having a storage phosphor bar code for identifying the storage phosphor;

x-ray exam bar code chart locatable with an x-ray source for identifying x-ray examination characteristics of said x-ray image stored in said storage phosphor, wherein said exam bar code chart includes sets of exam bar codes identifying unique body parts of a patient, x-ray exposure conditions, etc.;

hand-held bar code scanner having a user input, a memory, a digital controller, and a display, for scanning the patient bar code, the storage phosphor bar code and a bar code from at least one of said sets of bar codes on said exam bar code chart; and a required fields control card having bar codes representing required fields bar code scanner commands and bar codes representing required exam bar code sets to be scanned by a bar code scanner user.

DESCRIPTION OF THE DRAWINGS

FIGS. 5–7 are screens depicting some of the functions of a quality control station of the system of FIG. 4.

DESCRIPTION OF THE PREFERRED EMBODIMENTS

Figure 1:
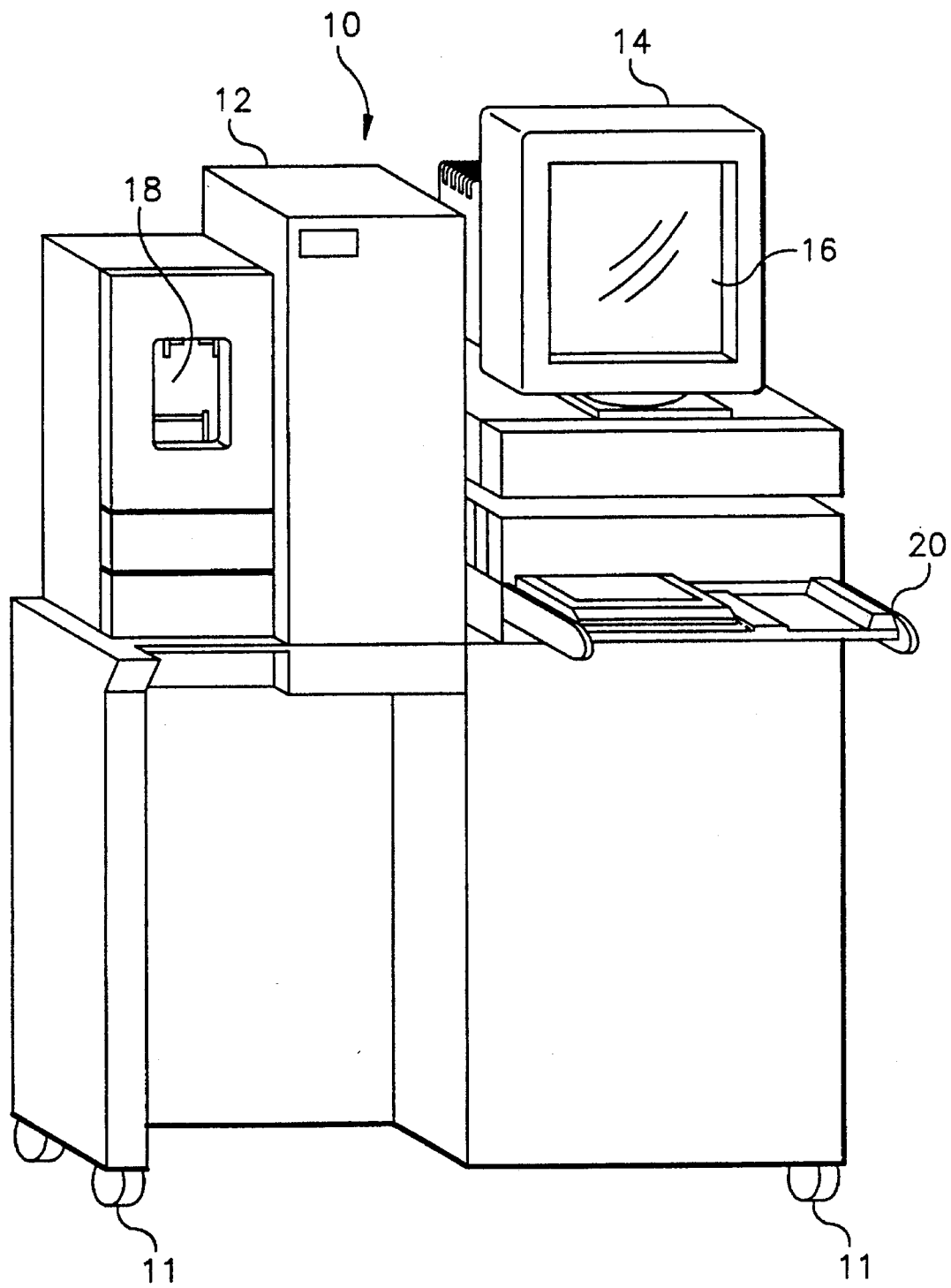
FIG. 1 is a perspective view of a storage phosphor reader.

Referring now to FIG. 1, there is shown a storage phosphor reader 10 incorporating an embodiment of the present invention. Reader 10 is mounted on casters 11 for easy portability in a radiology environment. Reader 10 includes a multiunit housing 12 housing the components of storage phosphor reader 10 and a video monitor 14 having a touch screen 16 supported on housing 12. Housing 12 also includes a bar code reader docking station 18 for docking a hand held bar code reader and for transferring data from the hand held bar code reader to storage phosphor reader 10. Reader 10 includes storage phosphor cassette load platform 20 which receives cassettes containing storage phosphor plates which are to be read or erased by reader 10.

In general, storage phosphor reader 10 processes images captured on a storage phosphor plate using conventional radiographic equipment. Reader 10 then scans the storage phosphor plate and converts the latent x-ray image therein into an electrical x-ray image signal which can be viewed on monitor 14. The scanned image is then delivered to a receiving device (such as a quality control station, laser printer or archival device) for image processing, image enhancement, viewing, printing and/or storage. The storage phosphor reader 10 is operated using touch screen 16 which also displays the image. The storage phosphor plates which are used to hold the unexposed x-ray images are mounted in standard size x-ray cassettes of different sizes. These storage phosphor plates can be erased and reused repeatedly. The optional hand held bar code reader can be used to collect exam information which is transferred to the storage phosphor reader 10 when it is mounted in station 18. The exam information is then associated with the scanned images.

As will be described in greater detail later, the storage phosphor reader 10 is used in storage phosphor patient identification system according to the present invention.

Following is a general description of a storage phosphor patient identification system.

When a radiology technologist receives a request for an x-ray examination of a patient, the technologist exposes a body part of the patient to an x-ray which is stored as a latent x-ray image in the storage phosphor plate of a storage phosphor cassette. Several images may be taken at this time. Using the optional portable bar code reader (scanner), the technologist scans the patient identification bar code label and the label on the storage phosphor cassette. Exam related information can be scanned from a bar code chart that is usually attached to the portable x-ray generator. Such information includes body part type, x-ray exposure conditions, position of patient and the like.

The image is now captured by the technologist performing the x-ray exam using the cassette containing the storage phosphor plate from which the bar code label was scanned. When the x-ray exam is complete the technologist takes the storage phosphor cassette to storage phosphor reader 10 to be processed. If the optional bar code reader is used, the technologist transfers the patient identification and exam information by inserting the bar code reader into the bar code reader station 18 on the front of reader 10. The scanned information is then transferred to the control system of the storage phosphor reader 10. The technologist then loads the cassette containing the exposed storage phosphor plate into reader 10 by loading on load platform 20. Scanning is initiated when the technologist presses a start button on touch screen 16.

Inside storage phosphor reader 10 the storage phosphor plate is extracted from the cassette and scanned with a laser light. As the plate is scanned, the image appears on touch screen 16 as it is being scanned. After the scanning is complete the image is sent to a receiving device where it can be tonescaled, enhanced, viewed, printed and/or stored. After the storage phosphor plate has been completely scanned it is erased by exposure to light which removes any remnants of the image. The storage phosphor reader 10 then places the storage phosphor plate back into its cassette. The technologist can now remove the cassette from reader 10 to be reused for another exam.

Figure 2:
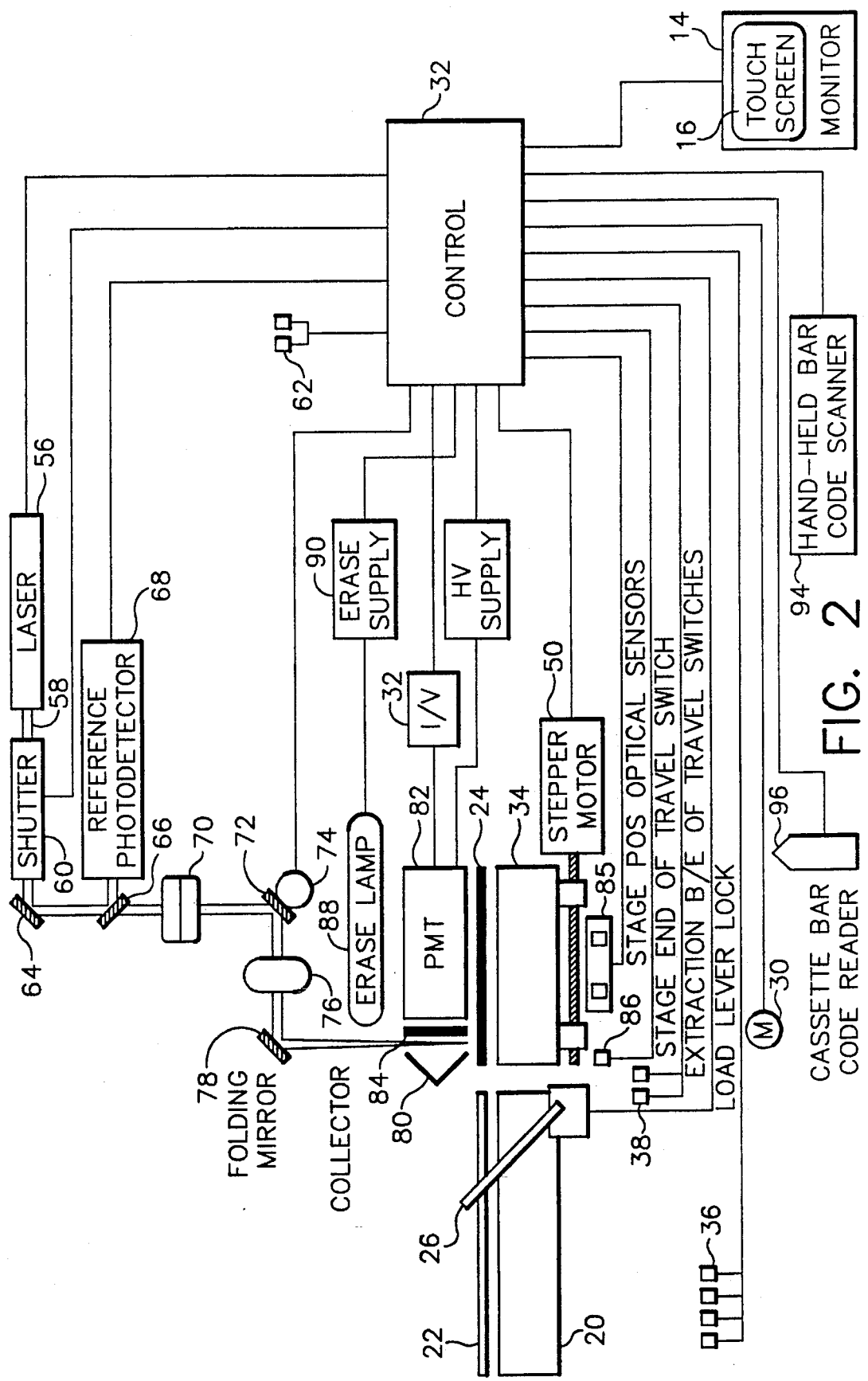
FIGS. 2 and 3 are respectively a partially diagrammatic, partially schematic view and a perspective view of the components of the storage phosphor reader of FIG. 1.
Figure 3:
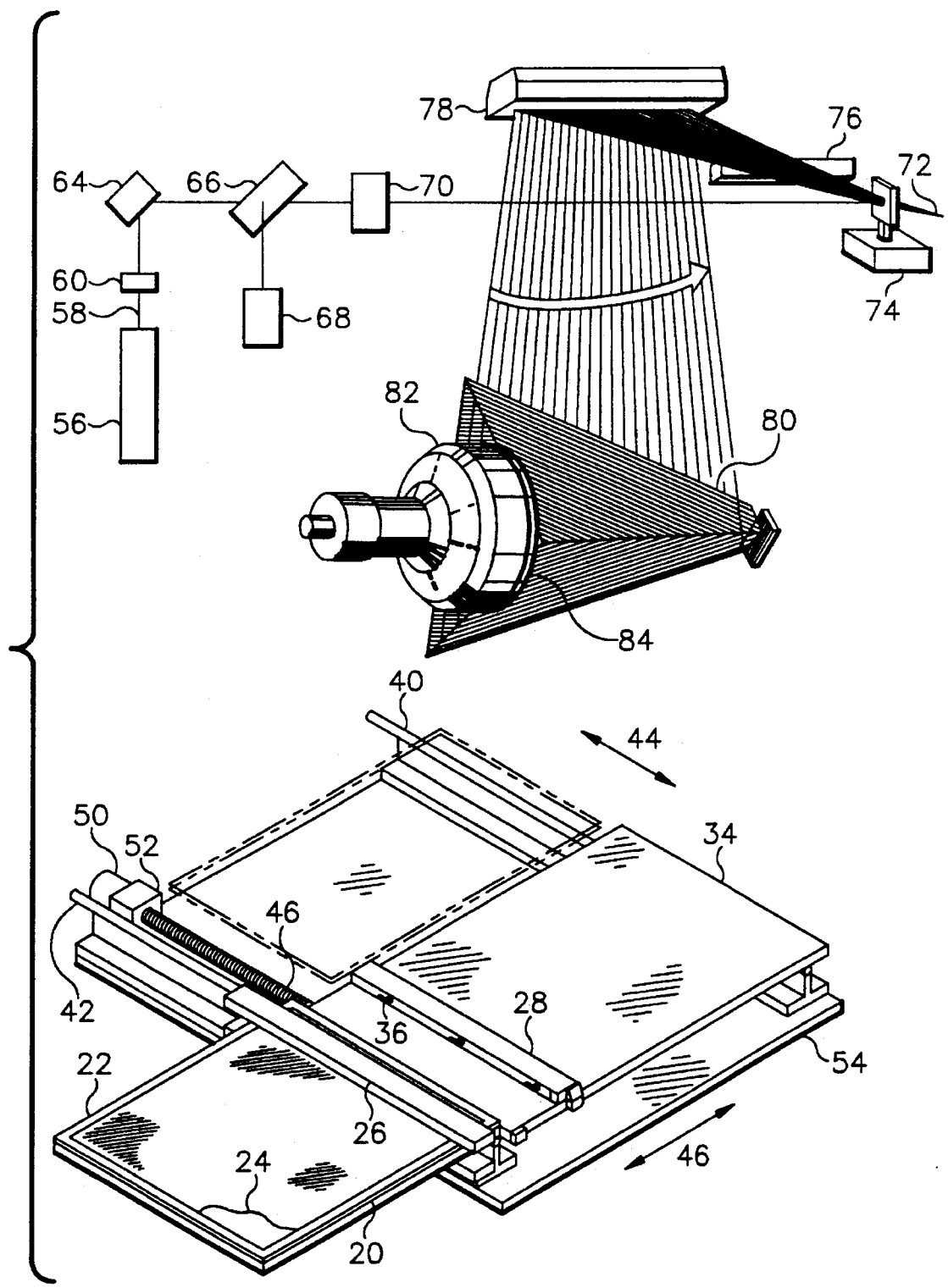

Referring now to FIGS. 2 and 3 there will be described in greater detail a preferred embodiment of storage phosphor reader 10. As shown, a storage phosphor cassette 22 containing a storage phosphor plate 24 is loaded on cassette load platform 20. Load lever 26 is rotated to clamp cassette 22 in place and to latch the cassette 22 to permit extraction of storage phosphor plate 24 therefrom. Storage phosphor plate 24 is extracted from cassette 22 by extraction device 28 (FIG. 3) which is actuated by extraction motor 30 under software control from control 32. Control 32 includes standard computer components such as a microprocessor, a magnetic disk drive for storing images, software applications and computer operating system and input and output devices to communicate with the components of reader 10. Such microcomputer systems are well known in the art and will not be described in detail herein.

Extraction device 28 is slidably mounted on translation stage 34 and includes hooks 36 which engage storage phosphor plate 24. Extraction device 28 extracts storage phosphor plate 24 from cassette 22 onto translation stage 34. As the storage phosphor plate 22 is loaded onto stage 34 it passes over plate size detecting switches 36 which detect the plate size and communicate this information to control 32. There are sufficient plate size detectors 36 to detect the different plate sizes that can be processed by reader 10. The beginning and end of travel of extraction mechanism 28 are sensed by extraction begin and end travel switches 38 connected to control 32.

Translation stage 34 is slidably mounted on rails 40 and 42 for movement in opposite directions 44 which are perpendicular to the directions 46 of loading and unloading of plate 24 relative to translation stage 34. Translation stage 34 is driven by a screw drive mechanism 48 actuated by stepper motor 50 mounted on block 52. Rails 40 and 42 are supported by frame member 54 of reader 10.

The laser scanning components will now be described. Reader 10 includes a laser 56 (such as a helium neon gas laser) for stimulation of storage phosphor plate 24. Laser 56 produces a laser beam 58 which passes through a shutter 60. Shutter 60 is controlled by digital signals received from control 32. Shutter 60 closes with activation of cover interlock switches 62 which detect closure of the housing 12 covers.

Beam 58 is reflected off mirror 64 and passes through beam splitter 66 which directs a portion of the laser beam 58 to reference photodetector 68. Following the beam splitter 66 laser beam 58 passes through collimator 70. The collimated laser beam is deflected by an oscillating scan mirror 72 driven by galvanometer 74 under the control of control 32. Scan mirror 72 provides the line scan raster motion of the laser beam 58. Galvanometer 74 drives mirror 72 with a constant angular velocity.

An f-theta lens 76 produces a flat field of focus and constant linear velocity at the plane of storage phosphor plate 24. Folding mirror 78 directs the laser beam through light collector 80 onto storage phosphor plate 24. Collector 80 may be of the type disclosed in commonly assigned U.S. Pat. No. 5,151,592, issued Sep. 29, 1992, inventors Boutet et al. The stimulating light of laser beam 58 causes the storage phosphor in plate 24 to emit light (blue) which is a function of the x-ray image stored in plate 24. Collector 80 directs this emitted light onto photomultiplier tube (PMT) 82. A filter 84 in front of the face of PMT 82 blocks the scattered stimulating laser light and passes the light emitted by storage phosphor plate 24. Once a storage phosphor plate 24 is on translation stage 34 a scan is begun. Movement of translation stage 34 in the direction of arrow 44 is under software control of control 32. Control 32 sends commands to stepper motor 50 to initiate a scan, to start translation stage 34, to start galvanometer 74 and to turn on PMT 82. From the home position of stage 34 the control 32 counts stepper motor 50 steps to the point where the storage phosphor plate 24 is under collector 80. At this point acquisition of the latent x-ray image on storage phosphor plate 24 begins. At the end of the scan (determined by the number of scan lines for the appropriate storage phosphor plate size), PMT 82 and galvanometer 74 are turned off and translation stage 34 is returned to the home position which is determined by one of the stage position optical sensors 85. A stage end of travel switch 86 is located just beyond the position of optical sensors 84 to prevent damage in case of failure of optical sensors 84.

Immediately after translation stage 34 reaches the home position, erase lamp 88 is turned on by actuation of erase power supply 90 under software control from control 32. Following a predetermined erase time (such as 30 seconds) erase lamp 88 is turned off and extraction mechanism 28 returns storage phosphor plate 24 in the direction of arrow 46 to storage phosphor cassette 22. When the extraction mechanism 28 trips the extraction end of travel switch 38, the lock for load lever 26 is released. The storage phosphor reader user can now rotate load lever 26 and remove cassette 22 from loading platform 20.

During the scan of storage phosphor plate 24 an emitted x-ray light image is converted by PMT 82 into an x-ray electrical current signal. This signal is converted to a voltage by amplifier 92. As described in greater detail in commonly assigned U.S. patent application Ser. No. 965,657, filed Oct. 23, 1992, inventor S. Dhurjaty, entitled "Noise Reduction in a Storage Phosphor Data Acquisition System", laser noise which is present in the x-ray image signal produced by PMT 82 is corrected by subtracting a reference signal detected by reference photodetector 68. The corrected digital signal is corrected for the light collection signature of light collector 80 by a correction lookup table in control 32. The correction lookup table is loaded during calibration of reader 10 when it is initially set up.

As will be described in greater detail later, patient identification and examination information are downloaded into reader 10 from a hand held bar code scanner 94 positioned in station 18 of reader 10. As each storage phosphor plate 24 is extracted from its cassette 22 cassette bar code reader 96 reads the bar code on plate 24. The image data and corresponding patient and exam information are correlated by control 32.

The physical size of the cassettes 22 containing the storage phosphor plates 24 are identical to that of conventional radiographic film/screen cassette sizes. Typically storage phosphor reader 10 is capable of reading the following storage phosphor plate sizes: 18×24 centimeters, 24×30 centimeters, 35×35 centimeters, and 35×43 centimeters. The raster pattern or matrix pixel size for each storage phosphor plate that can be processed is, for example, as follows: 18×24 cm - 1792×2400; 24×34 cm - 2048×2500; 35×35 cm - 2048×2048; and 35×43 cm - 2048×2500.

The storage phosphor reader 10 of FIG. 1 can be part of a critical care system made up of hardware and software that allows radiology technologists to (1) capture images onto a standard cassette which contains a storage phosphor plate using the sites conventional x-ray image capture methods; (2) convert those images into electronic images using the storage phosphor reader 10; (3) using a quality control workstation correct any erroneous patient information, exam information, and, if necessary, the x-ray image look; (4) print the image and its text label on an x-ray laser printer; and (5) enter patient information into the patient database and generate a bar code label for the patient identification. Optionally, the critical care system also allows a requesting physician or radiologist to view the image on a high resolution workstation, such as the Personal Display System supplied by Vortech, of Richardson, Tex. The system can also be expanded to allow optional permanent archiving of x-ray exams on optical disk where it can be retrieved for later viewing or reprinting.

Figure 4:
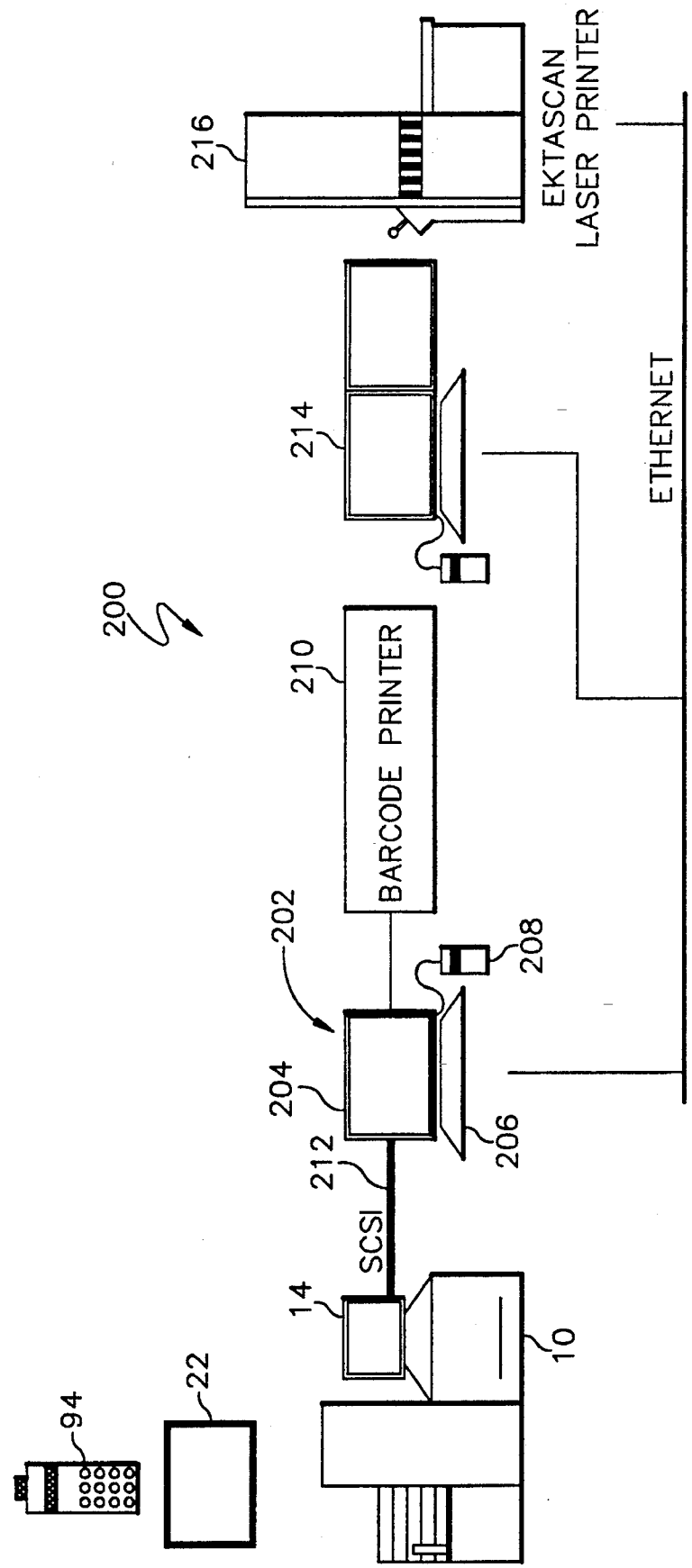
FIG. 4 is a schematic diagram of a critical care system incorporating the present invention.

Referring to FIG. 4, there is shown a diagrammatic view of a critical care system incorporating an embodiment of the present invention. As shown, critical care system 200 includes storage phosphor reader 10 having a control and viewing monitor 14. Reader 10 accepts storage phosphor x-ray cassette 22 for converting an x-ray image in the cassette storage phosphor into a digital x-ray image. A hand-held bar code scanner 94 is provided to download patient ID and exam information into reader 10. System 200 also includes quality control and data entry workstation 202 which includes a high resolution monitor 204, a data entry keyboard 206, and a mouse 208. An optional bar code printer 210 is linked to quality control workstation 202. Storage phosphor reader 10 communicates with work station 202 by means of a communication channel, such as a SCSI communications link 212.

Link 212 passes a raw digital x-ray image from storage phosphor reader 10 to quality control workstation 202. Workstation 202 allows a technologist to view the x-ray image. It also functions as the database server, upon which the demographic database resides. Workstation 202 will be described in greater detail hereinafter, but, in general, provides an interactive data entry interface for the technologist and prints patient ID bar code labels on bar code printer 210. Using the quality control workstation 202, the radiology technologist can modify the image presentation (orientation, tonescale, edge enhancement) and patient or examination information prior to approving the image and routing it to its next destination. The technologist can also modify or add routing information for a patient for a single image.

Quality control workstation 202 can be used in a pass-through mode or a manual mode. In pass-through mode, x-ray exams are processed at the workstation 202 and then routed directly to other destinations, such as high resolution PDS 214, or laser printer 216 (such as a Kodak Ektascan Laser Printer). In manual mode, a user must verify the x-ray image from reader 210 and patient and exam information before releasing it to its destination. The image enhancement which allows for proper display of the images for diagnostic purposes is performed by adaptive unsharp masking processing and tonescaling. The tonescaling algorithms are preferably those described in U.S. patent application Ser. No. 797,615, filed Nov. 25, 1991, inventors Capozzi and Schaetzing, entitled "Method and Apparatus for Automatic Tonescale Generation in Digital Radiographic Images" and U.S. patent application Ser. No. 906,191, filed Jun. 29, 1992, inventors Jang and Schaetzing, entitled "Method for Automatic Foreground and Background Detection in Digital Radiographic Images".

Quality control workstation 202 is linked to high resolution personal display system 214 and laser printer 216 by means of a communication link, such as an Ethernet link. This link may be a hard wire or optical linelink, or a wireless link, or a satellite link.

In general, quality control workstation 202 has sufficient resident memory and fixed disk storage to meet the following requirements: (1) storage of a predetermined number of x-ray exams, (2) patient database, (3) exam information (such as exposure conditions, body part, patient position, etc.), (4) preference information, i.e., image processing parameters for exam types, (5) error and transaction logs, (6) an operating system, (7) application software.

In general, the quality control workstation 202 provides the radiology technologist with the following functions:

1. Check images acquired from storage phosphor reader 10.

2. Correct patient information and x-ray exam information.

3. Adjust image parameters, such as image orientation and window width and level (after they have been automatically enhanced using tonescaling and unsharp masking techniques in workstation 202).

4. Route an acceptable exam or image (automatically or by specification) to one or more destinations such as an x-ray laser printer, a viewing station (PDS) or image archive. In manual mode, the exam must be approved (released) by the technologist before it will be automatically routed to a specified or default destination. Preferably, the image data is transmitted to its destination in a ACR-NEMA (America College of Radiology-National Electrical Manufacturers Association) file which contains the processed image data and ACR-NEMA header (containing patient information and exam information) and applicable look-up tables.

5. Automatically process exams and route them directly to the destinations. This is called pass-through mode.

6. Enter patient information (demographics) into the local (i.e., critical care system) patient database, or access the system patient database.

7. Generate bar code labels for each newly acquired patient identification number and, as necessary, new bar code labels required for the exam data collection card and, optionally, radiology technologist identification.

Figure 5:
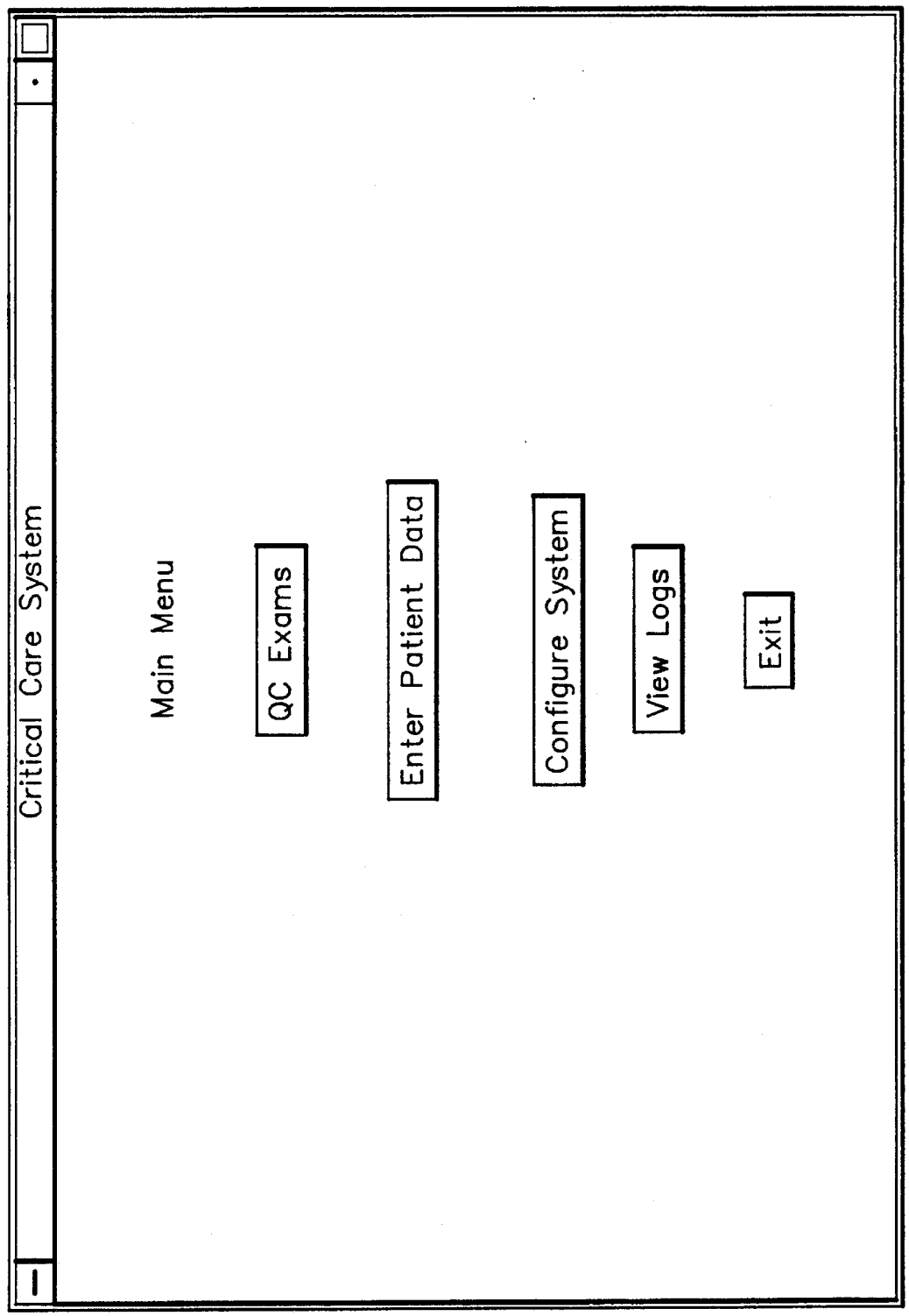

The enumerated functions of quality control workstation 202 are described in greater detail in commonly assigned U.S. patent application Ser. No. 981,144, filed Nov. 24, 1992, inventor Godlewski et al. Only the features which are important to an understanding of the present invention will be described now. As shown in FIG. 5, the main menu is used to select the quality control function to be used. Main menu shown in FIG. 5 includes the selectable functions QC exams, enter patient data, configure system, view logs, exit.

Figure 6:
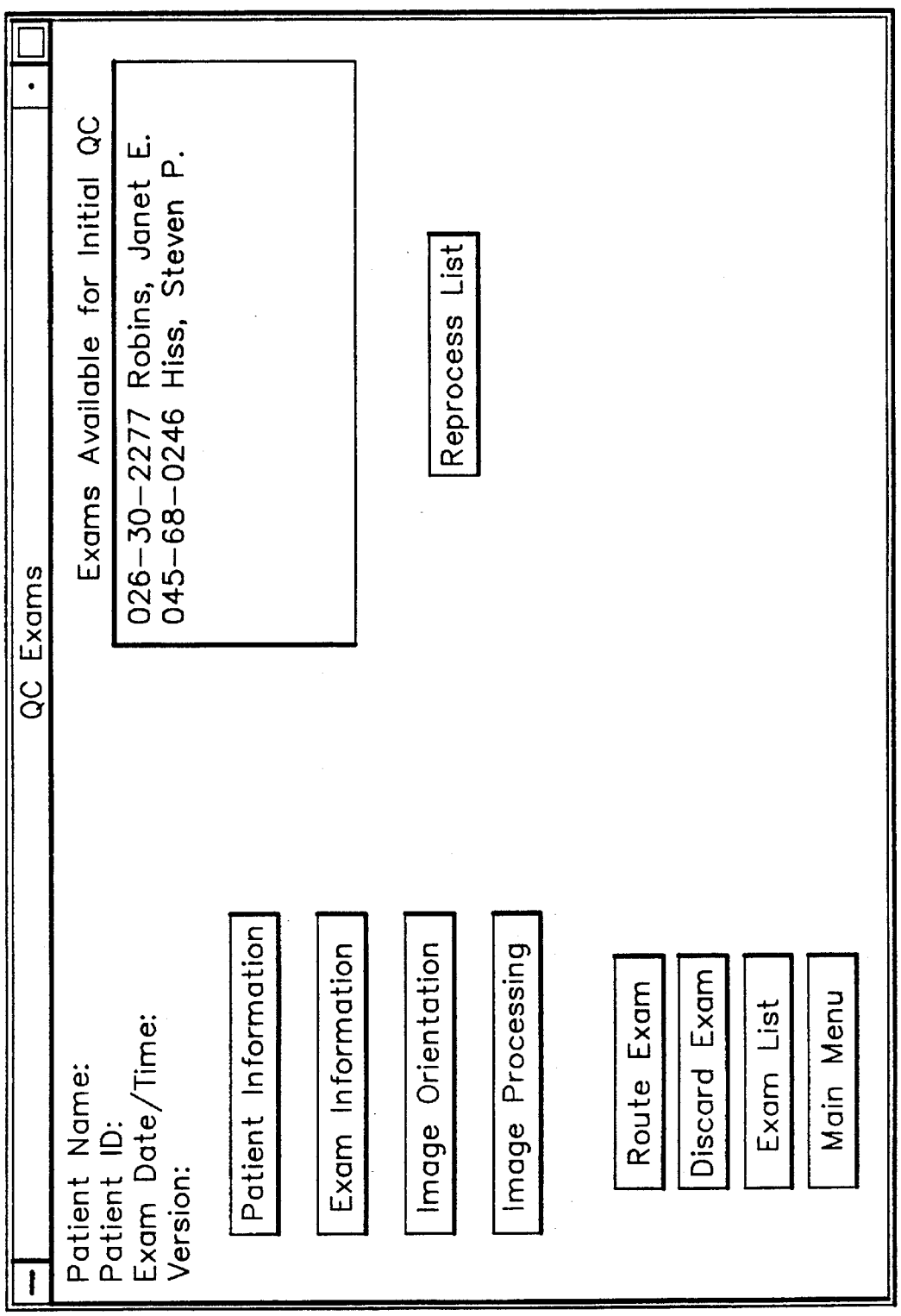

FIG. 6 depicts the QC exams screen with the exams (images) which are available for initial quality control processing. Two exams are listed for ROBBINS and HISS. This screen also indicates several other function buttons which can be selected, i.e., a reprocess list, patient information, exam information, image orientation, image processing, route exam, discard exam, exam list, and main menu.

Figure 10:
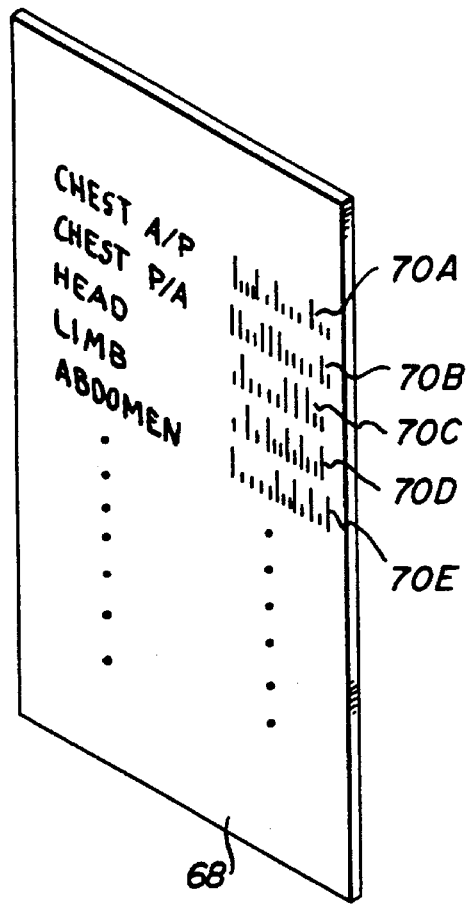
FIG. 10 is a diagrammatic view of an x-ray exam type chart shown in FIG. 8.
Figure 11:
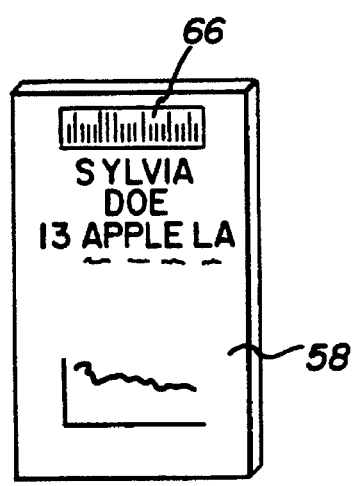
FIG. 11 is a diagrammatic view of a patient ID chart shown in FIG. 8.

Referring to FIG. 7, the screen shown is the QC exam screen with patient information window. The patient information window is displayed when the patient information button, shown in FIG. 10, is selected. The patient information window shows the following patient information, i.e., patient name, patient ID, date of birth, patient sex, radiologist, referring physician, room/unit number, bed number, hospital, department, diagnosis, and destinations. The process buttons in the lower left-hand corner are update, reset and done. The operator of QC workstation can enter, verify or change the patient information with this screen displayed.

Figure 8:
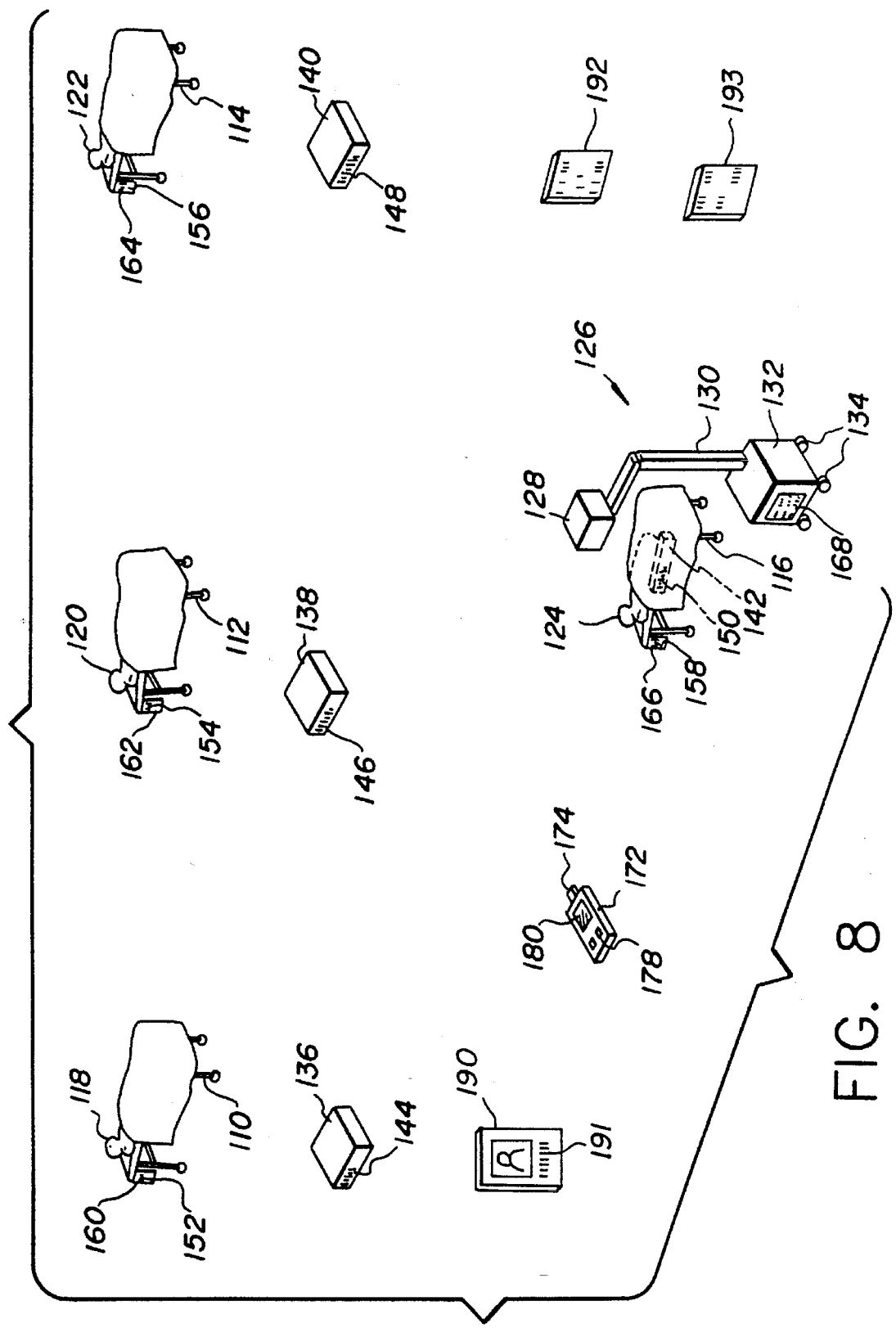
FIG. 8 is a perspective view of a medical care facility incorporating an embodiment of the present invention.

Referring now to FIG. 8, there will be described an embodiment of the present invention as used in a multi-bed medical care facility such as the intensive care unit of a hospital. As shown, the medical care facility includes a plurality of beds 110, 112, 114, and 116 having respective patients 118, 120, 122, and 124 who require medical treatment. A mobile X-ray unit 126 has an X-ray source 128 mounted on a moveable arm 130 supported by cabinet 132. Cabinet 132 includes controls and power supply for X-ray source 128. Wheels 134 on cabinet 132 facilitate moving unit 126 from bed to bed.

According to the present invention, an X-ray image of a body part of a patient is produced in a stimulable storage phosphor contained in a cassette. Thus, storage phosphor cassettes 136, 138, 140, and 142 are provided for patients 118, 120, 122, and 124, respectively. Cassettes 136, 138, 140, and 142 have storage phosphor identifying bar codes 144, 146, 148 and 150 which uniquely identify each storage phosphor.

Figure 9:
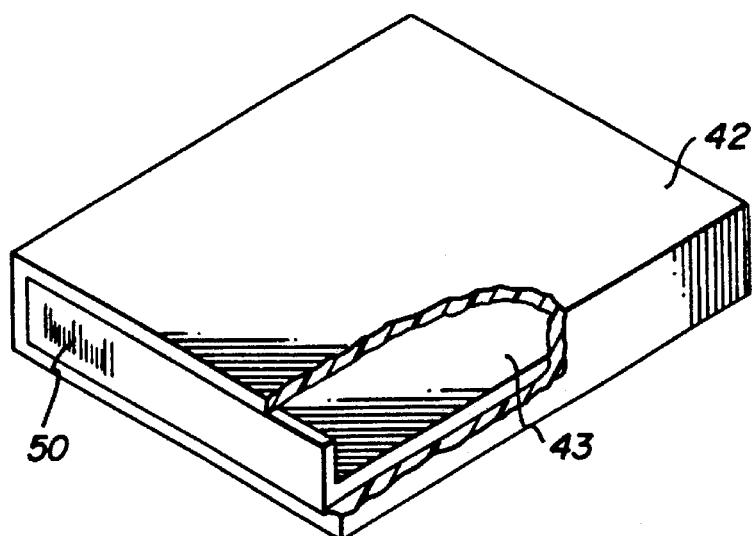
FIG. 9 is a partially broken away perspective view of a storage phosphor cassette shown in FIG. 8.

As shown in FIG. 9, storage phosphor cassette 142 has a removable storage phosphor plate 143 with bar code 150. An exemplary storage phosphor cassette is disclosed in commonly assigned, copending U.S. application Ser. No. 617, 121.

Each patient 118, 120, 122, and 124 is provided a unique patient identifying bar code 152, 154, 156, and 158 on respective patient charts 160, 162, 164, and 166. X-ray unit 126 has associated with it a chart 168 having a list of X-ray exam types and/or X-ray exposure conditions with a set of bar codes identifying each exam type and exposure condition. As shown in more detail in FIG. 10, chart 168 has a list of X-ray exam types, such as, chest P/A (Posterior/Anterior); chest A/P (Anterior/Posterior); head; limb; abdomen, etc. Each X-ray exam type has a unique identifying bar code, 170A, 170B, 170C, 170D, 170E, etc. As shown in FIG. 8; a default values control card 192 and a required fields control card 193 are also provided and will be described in greater detail later.

According to the technique of the present invention, an X-ray technologist who is responsible for taking X-rays at the medical care facility is provided with a portable bar code scanner 172. The technologist has a badge 190 with a technologist identifying bar code 191. Bar code scanner 72 (see FIG. 12) has a light scanner 174 for scanning bar codes and converting the scanned bar code into an electrical signal which is stored in memory 176. Preferably, scanner 172 has a keyboard 178 for entering data which is stored in memory 176 and also has a display 180 for displaying the input data and other information. Control circuit 173, scanner 174, memory 176, display 180 and keypad 178 are internally connected by bus 182. A communications adapter 179 allows communication with storage phosphor reader 10.

In general, at the time a patient is exposed to an X-ray, a technologist scans the technologist identifying bar code, scans the patient identifying bar code, scans the storage phosphor identifying bar code(s) and scans the bar codes identifying the X-ray exam type. Thus, for example, as shown in FIG. 8, X-ray source 128 is positioned over patient 124 and storage phosphor cassette 142 is positioned under the chest area of patient 124. At the time of taking an X-ray, the technician uses bar code scanner 172 to scan patient identifying bar code 166 on patient chart 158, to scan storage phosphor identifying bar code 150 on storage phosphor cassette 142, and to scan X-ray examination type bar code 170A on exam type chart 168. Bar code 170A identifies the X-ray exam type as a chest Anterior to Posterior exam. Chart 168 may also contain other information relating to the X-ray examination, such as, X-ray exposure conditions, patient position, etc., which are also scanned by bar code scanner 172 and stored in memory 176. A technician identifying bar code may also be read. The technician can correct or manually enter data via keypad 178 at the time an X-ray exam is effected.

After the technician has finished an X-ray exam of patient 124, he can move X-ray unit 126 to the bedside of patients 118, 120, and 122 to produce X-ray images in storage phosphor cassettes 136, 138, and 140.

After a set of X-ray exposures have been taken and relevant data for each exposure scanned and stored in memory 76 of portable bar code scanner 172, the technician carries the storage phosphor cassettes 136, 138, 140, and 142 in a stack to storage phosphor reader 10 (FIG. 1).

In general, according to the present invention, there is provided a bed side Exam Data Collection System used to collect, store and communicate all of the required data associated with a particular patient exam with its matching image.

Figure 12:
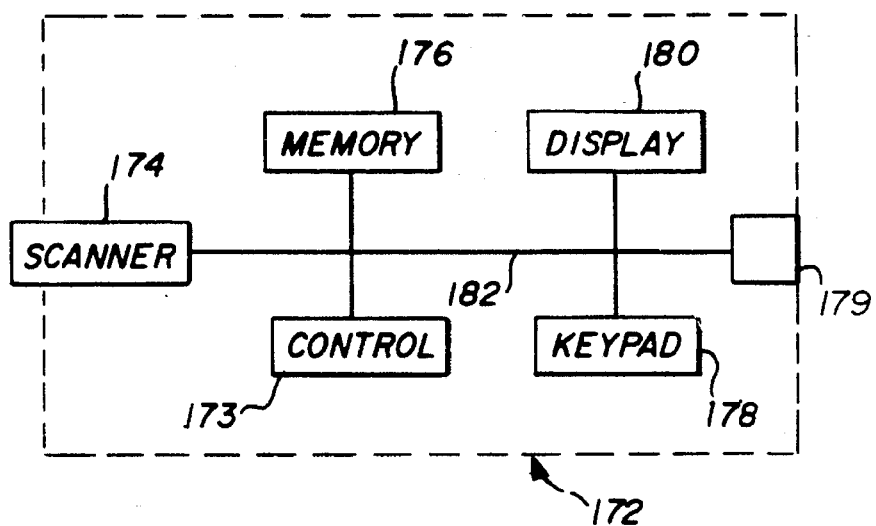
FIG. 12 is a block diagram of the bar code scanner of FIG. 8.
Figure 13:
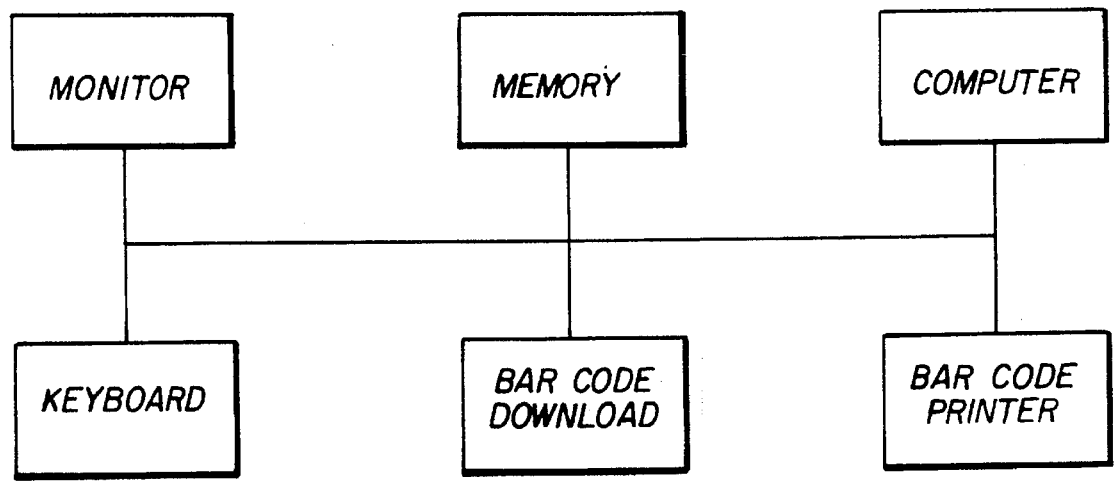
FIG. 13 is a block diagram of the system of FIG. 1.

The means of performing these functions is with the use of: bar code labels, a bar code scanner 172, a communications adapter 179, an Exam Data Collection Card 168, a Default Values Control Card 192, a Required fields Control Card 193. The bar code scanner 172 is a self contained, hand held system which has its own memory, micro controller and power source (FIG. 12). Data and comments are entered into the bar code scanner by scanning the bar code labels associated with the appropriate information or by typing the information on an alphanumeric keypad located on the bar code scanner. The bar codes may be found in various locations including: patient beds and charts 110–116, technologist identification badges 190, on the storage phosphor cassettes 136–142, on the Site specific Exam Data Collection Card 168, on the Default Values Control Card 192, on the Required Fields Control Card 193.

The Exam Data Collection System provides the following functions:

1. The means for the technologist to collect exam data.
2. The means to set the date and time.
3. The means to transfer the exam data to reader 10.
4. The means to specify the minimum required data fields for each exam.
5. The means to specify the default values for nonrequired data fields.
6. The means to accept software changes which will effect the systems functionality or performance.
7. The means to indicate error conditions that may occur during the normal operation of collecting or transmitting data.
8. The means to delete a complete exam data record for a cassette.
9. The means to designate a cassette to be erased (Flash or Full). This requirement is essential with small cassette sizes.

The bar code scanner 172 will provide the means of collecting exam data for use by the system. The fields collected are:

1. Date and Time of exam—provided by the bar code scanner.
2. Requisition number.
3. Patient identification number.
4. Technologist identification number.
5. Cassette identification number.
6. Cassette orientation used during exam.
7. Projection used during exam.
8. Body part of patient exposed.
9. Position of the patient.
10. Distance of the exposure.
11. KVP of the exposure.
12. MAS of the exposure
13. Comments entered during data collection.

The exam data can be entered in any order and may be changed as many times as necessary by simply entering a new value for the field of interest. The bar code scanner 172 will continue in this manner for a single patient record until the PATIENT RECORD COMPLETE bar code has been selected from the Exam Data Collection Card 168. The data fields collected may be reviewed at any time during the collection process by selecting the REVIEW PATIENT RECORD bar code from the Exam Data Collection Card 168.

Data entry is accomplished by either selecting a bar code or through the alphanumeric keypad. The entries into the bar code scanner 172 are kept in RAM and are separated into distinguishable fields according to the unique preface associated with each bar code field. The current patient record is located in a temporary buffer separate from any other exams which may have already been completed and accumulated into a file for ultimate transfer to reader 10.

Upon recognition of either a data bar code or the ENTER xx bar code, the software will interpret the input to decide what action must be taken. If the input is not associated with some system action (exit to system, send data to reader 10, review data, etc.) the data will be written into the temporary buffer associated with that field and overwriting any data that had previously been entered. The entry will then be passed through an internal lookup table to translate the received bar code value into an alphanumeric response which will be displayed on the bar code scanner LCD display panel.

While entering data via the keyboard, the user may use the BACKSPACE key to delete the last character entered or the DELETE key to delete the entire entry.

The bar code scanner software will provide the means of reviewing all of the data collected for the currently open patient record. This is accomplished by selecting the REVIEW PATIENT RECORD bar code from the Exam Data Collection Sheet 68. All of the data recorded for the current patient will be displayed, one field at a time, at approximately one second intervals. The order of display during review is: Cassette ID, Patient ID, Tech ID, Projection, Body part, Position, Distance, KVP, mAs, Orientation, Requisition# and Comments.

The bar code scanner software will keep each new patient record separate until the PATIENT RECORD COMPLETE bar code is scanned in from the Exam Data Collection Card. If the minimum required fields for the record are present, the bar code scanner software will store the completed record in the main storage file which will contain all of the exam records that have been collected for their eventual transfer to reader 10.

The bar code scanner software will close and move the current patient record to the main file buffer upon the selection of the PATIENT RECORD COMPLETE bar code from the Exam Data Collection Sheet. However, the bar code scanner software will only complete the current patients record if entries have been made into each of the required fields currently specified. If all of the required fields do not have entries, the bar code scanner software will prompt the user for input by displaying the fields, one at a time, that are necessary to complete the record. Once the required fields have been entered, the bar code scanner software will stop prompting for more input and close the current patient record as described above.

The bar code scanner software will save the Patient Identification Number associated with the currently open record. There are two methods to input the Patient ID.

1. Free form Patient ID: This allows the use of bar codes generated by external RIS systems. The bar codes must conform to those supported by the bar code scanner. In this case, the technologist must first scan the ENTER PATIENT ID bar code from the Exam Data Collection Card. Then the Patient ID may be scanned, or the keypad may be used to enter the Patient ID. The keypad defaults to alphabetical mode.

2. Encoded Patient ID: This allows the Patient ID to be directly scanned without any previous steps. This method is expected to be used by the customers who use the QCW to generate the patient ID bar code. The Patient ID bar bode must be in code 39 and must be encoded with the character $ preceding the actual patient ID. This will identify it as a patient ID. The scanner software removes the $ character before passing the patient ID to reader 10.

The maximum number of characters that can be accepted as patient identification is 15 alphanumeric.

The bar code scanner software will save the Technologists Identification associated with the currently open record. There are two methods to input the Technologist ID.

1. Free form Technologist ID: This allows the use of bar codes generated by external RIS systems. The bar codes must conform to those supported by the bar code scanner. In this case, the technologist must first scan the ENTER TECHNOLOGIST ID bar code from the Exam Data Collection Card. Then the Technologist ID may be scanned, or the keypad may be used to enter the Technologist ID. The keypad defaults to alphabetical mode.

2. Encoded Technologist ID: This allows the Technologist ID to be directly scanned without any previous steps. This method is expected to be used by the customers who use the QCW to generate the Technologist ID bar code. The Technologist ID bar code must be in code 39 and must be encoded with the character % preceding the actual Technologist ID. This will identify it as a Technologist ID. The scanner software removes the % character before passing the Technologist ID to reader 10.

The maximum number of characters that can be accepted as technologist identification is 15 alphanumeric.

The bar code scanner software will save the Requisition Number associated with the currently open record. The data is entered from the bar code scanner keypad, however, the ENTER REQUISITION# bar code must be selected prior to bar coding the requisition# or entering the numbers with the keypad. The keypad defaults to numeric entry.

When using the keypad, the CARRIAGE RETURN key must be pressed after the numbers have been entered. The maximum number of characters that can be accepted as requisition number is 15 alphanumeric.

The bar code scanner software will provide the means of accepting one comment for each patient exam record. The maximum length that this comment can be is 31 characters. The ENTER COMMENTS bar code must be selected prior to entering a comment. The keypad is used for entry of any comments associated with an exam, at the completion of the entry of the desired comment the user must press the CARRIAGE RETURN key of the bar code scanner.

The Exam Data Collection Card will provide some fixed comment bar codes which will allow the user to bar code comments by selecting the appropriate comment. An example of fixed comments are:

1. Patient Moved
2. Patient Large
3. Patient Small
4. Patient Uncooperative

The bar code scanner will include the date and time that each patient record was completed and stored in its internal buffer.

The bar code scanner software will support record deletion. Two methods of record deletion are supported depending on whether the user wishes to delete a record that has been completed or one that is still open.

When a cassette ID is entered, for which a data record exists in the scanner's buffer, the user will be prompted with a message that the cassette is in use and a menu selection is presented.

The user may choose to reuse the cassette: the old record is deleted and the cassette ID is associated with the currently open record.

Alternatively, the user may select not to reuse the cassette: the bar code scanner prompts the user for a valid cassette ID to continue the current record.

There is a bar code on the Exam Data Collection Card labeled CLEAR CURRENT EXAM. This bar code can be used in the event that the technologist needs to completely remove the currently open record. The currently open record will be removed, but no others.

Transfer of data can be initiated by placing the scanner in the communications adapter cradle and pressing the SEND key.

The bar code scanner will provide the necessary header and trailer to the data and the necessary tabs, carriage returns and line feeds between the individual fields. Upon the completion of the transfer of all the exam data to reader 10 and upon receipt of a data received response, the bar code scanner will free its memory for the storage of new exam data.

The bar code scanner will initially require only those fields which are set at the factory as required fields. They are:

1. Cassette number
2. Patient identification number
3. Data and time of patient exam—provided by the bar code scanner.

Using the REQUIRED FIELDS CONTROL CARD, the user may specify additional required data fields that the technologist must enter for each exam.

During the exam data collection, the required fields must be read into the bar code scanner before it will allow a record to be completed.

To use any of the Required fields commands the user must be in Exam data mode with no currently open records.

To configure the required fields, the user first scans the SELECT REQUIRED FIELDS bar code from the REQUIRED FIELDS CONTROL CARD, this causes the required fields to be reinitialized to factory defaults. The user then scans the desired required fields, and finally, scans the STORE REQUIRED FIELDS & EXIT bar code from the REQUIRED FIELDS Control Card. The Required Fields remain valid until they are re-entered or until new code is downloaded to the bar code scanner.

The required fields that are currently active in the bar code scanner may be reviewed at any time by selecting the REVIEW REQUIRED FIELDS bar code from the Special Functions Control Card.

The factory default required fields may also be stored in the bar code scanner at any time by selecting the SET REQUIRED FIELDS TO FACTORY DEFAULT bar code from the Control Card.

Using the DEFAULT VALUES CONTROL CARD, the user may set the default values they wish for their site. Default values may be specified for body part, projection, distance, KVP, mAs, Patient position and cassette orientation.

To use any of the Default Values commands, the user must be in Exam data mode with no currently open records.

To set the default values, the user scans the SELECT DEFAULT VALUES bar code from the control card, this causes the old defaults to be erased. The user may then scan the desired defaults from the control card, as if collecting exam data. Fields may be entered in any order and can be re-entered to correct errors. To store the defaults, the user scans the STORE DEFAULT VALUES AND EXIT bar code. This causes the bar code scanner to store the defaults for use during exam data collection. The defaults remain valid until they are re-entered or until new code is downloaded to the bar code scanner.

To review the default values, the user scans the REVIEW DEFAULT VALUES bar code at any time. The defaults are displayed, one at a time at approximately one second intervals.

The user may also scan the SET DEFAULT VALUES TO FACTORY DEFAULTS bar code at any time. This causes all defaults to be erased.

During exam data collection, if the technologist does not enter a field, the bar code scanner uses the default value set for that field (as long as it is not a required field). If no default is specified, the factory default is used. The factory defaults are NO DATA.

The bar code scanner will read the following standard bar codes, for example:

1. EAN/UPC-A and E
2. CODE39
3. CODABAR
4. Interleave 2 of 5
5. CODE 128.

The EXAM DATA COLLECTION CARD is created for each site, depending on the site's needs. A default EXAM DATA COLLECTION CARD is provided as a publication with the Exam Data System.

The EXAM DATA COLLECTION CARD is used by the technologist at bed side to enter all the relevant exam data.

The following bar codes and corresponding field values may appear on the Exam Data Collection Card 68. The Field Value is the text that should appear above the bar code for easy viewing while scanning. For each Field Value, the actual information to encode into the bar code is given in the Bar Code column.

All the bar codes on the EXAM DATA COLLECTION CARD should be in Code 39.

TABLE 1

| Field | Field Values | Bar Code |
| --- | --- | --- |
| Projection | AP | PR01 |
|  | PA | PR02 |
|  | Lateral | PR03 |
|  | RLD | PR04 |
|  | LLD | PR05 |
|  | RL | PR06 |
|  | LL | PR07 |
|  | RLO | PR08 |
|  | LLO | PR09 |
|  | Other Projection | PR00 |
| Body Part | Chest | BP01 |
|  | Abdomen | BP02 |
|  | Skull | BP03 |
|  | CSpine | BP04 |
|  | Pelvis | BP05 |
|  | TSpine | BP06 |
|  | Clavicle | BP07 |
|  | Breast | BP08 |
|  | LSpine | BP09 |
|  | Hip | BP10 |
|  | Other Body Part | BP00 |
| Patient Position | Supine | PO01 |
|  | Semierect | PO02 |
|  | Erect | PO03 |
|  | Other Position | PO00 |
| Distance | xx inches | DIxx |
|  | xxx inches | DIxxx |
|  | Enter Distance | DI00 |
| KVP | xx KVP | KVxx |
|  | xxx KVP | KVxxx |
|  | Enter KVP | KV00 |
| MAS | x.x mAs | MAx.x |
|  | x.xx mAs | MAx.xx |
|  | x mAs | MAx |
|  | xx mAs | MAxx |
|  | Enter mAs | MA00 |

TABLE 1-continued

| Field | Field Values | Bar Code |
| --- | --- | --- |
| Plate Orientation | Landscape | OR01 |
|  | Portrait | OR02 |
|  | Other Orientation | OR00 |

In addition to these data fields, there are control codes that will make the Hand Held input system easier to use. They are not tied to any particular field.

| Control Commands | Bar Code |
| --- | --- |
| Review Patient Record | CT01 |
| Patient Record Complete | CT02 |
| Reserved | CT03 |
| Delete Current Exam | CT04 |
| Enter Commands | Bar Code |
| Enter Comments | EN01 |
| Enter Technologist ID | EN02 |
| Enter Patient ID | EN03 |
| Enter Requisition Number | EN04 |
| Fixed Comments | Bar Code |
| Patient Moved | CM01 |
| Patient Large | CM02 |
| Patient Small | CM03 |
| Patient Uncooperative | CM04 |

The required Fields Control Card is provided as a publication with the Exam Data System. It is used by the Technologist or administrator to customize the required fields as described above.

The following codes appear only on the Required Fields Control Card.

TABLE 2

| Field | Bar Code |
| --- | --- |
| Set Required Fields to Factory Default | RF00 |
| Review Required Fields | RF01 |
| Select Required Fields | RF02 |
| Store Required Fields & Exit | RF03 |
| Projection Required | RF04 |
| Body Part Required | RF05 |
| Patient Position Required | RF06 |
| Distance Required | RF07 |
| KVP Required | RF08 |
| MAS Required | RF09 |
| Orientation Required | RF10 |
| Comments Required | RF11 |
| Tech ID Required | RF12 |
| Requisition # Required | RF13 |

TABLE 3

| Field | Field Values | Bar Code |
| --- | --- | --- |
| Set Default Values to Factor Default |  | DV00 |
| Review Default Values |  | DV01 |
| Select Default Values |  | DV02 |
| Store Default Values & Exit |  | DV03 |
| Projection | AP | PR01 |
|  | PA | PR02 |
|  | Lateral | PR03 |
|  | RLD | PR04 |
|  | LLD | PR05 |
|  | RL | PR06 |
|  | LL | PR07 |
|  | RLO | PR08 |
|  | LLO | PR09 |

TABLE 3-continued

| Field | Field Values | Bar Code |
|---|---|---|
| | Other Projection | PR00 |
| Body Part | Chest | BP01 |
| | Abdomen | BP02 |
| | Other Body Part | BP00 |
| Patient Position | Supine | PO01 |
| | Semierect | PO02 |
| | Erect | PO03 |
| | Other Position | PO00 |
| Distance | Enter Distance | DI00 |
| KVP | Enter KVP | KV00 |
| MAS | Enter mAS | MA00 |
| Plate Orientation | Landscape | OR01 |
| | Portrait | OR02 |
| | Other Orientation | OR00 |

The communications is accomplished over an RS-232 serial link between the bar code scanner cradle and reader 10. Communication is initiated by placing the bar code scanner into its cradle with the power switch on and selecting the SEND key. The bar code scanner opens the communications port. This will establish a communications link between reader 10 and the bar code scanner.

The following is the sequence in which data must be transferred from the bar code scanner to reader 10. Data fields must be delineated with a <Tab> and must be sent in the order shown to be properly understood by reader 10. If data is not available for a particular field just the <Tab> field delimiter must be sent. If a particular field is a reader 10 required data field, the table will state (REQUIRED FIELD) in the default column. Records begin with "\" and end with <CR> <LF>. The file must end with "&". @KODAK <CR> <LF>= beginning of file #### RECORDS <CR> <LF>= number of records in the file

| EXAM DATA | Max Size | DEFAULT VALUE |
|---|---|---|
| \ | | Record starts with "\" |
| Cassette ID # <Tab> | 15 characters | REQUIRED FIELD |
| Technologist ID #1 <Tab> | 15 characters | <Tab> |
| Reserved <Tab> | 15 characters | <Tab> |
| Patient ID <Tab> | 15 characters | REQUIRED FIELD |
| Projection <Tab> | 15 characters | <Tab> |
| Body Part <Tab> | 15 characters | <Tab> |
| Orientation <Tab> | 15 characters | <Tab> |
| Distance <Tab> | 15 characters | <Tab> |
| KVP <Tab> | 15 characters | <Tab> |
| MAS <Tab> | 15 characters | <Tab> |
| Comments <Tab> | 31 characters | <Tab> |
| Date <Tab> | 15 characters | REQUIRED FIELD |
| Time <Tab> | 15 characters | REQUIRED FIELD |
| Requisition # <Tab> | 15 characters | <Tab> |
| Position <Tab> | 15 characters | <Tab> |
| <CR> <LF> | | Record ends with <CR> <LF> |
| & | | file ends with ampersand |

All fields are variable size, delimited by tabs and no padding is used.

What is claimed is:

1. A patient identification and x-ray exam data collection bar code system, comprising:

a patient bar code located with a patient for identifying a patient;

a storage phosphor for storing an x-ray image of a patient, said storage phosphor having a storage phosphor bar code for identifying the storage phosphor;

x-ray exam bar code chart locatable with an x-ray source for identifying x-ray examination characteristics of said x-ray image stored in said storage phosphor, wherein said exam bar code chart includes fields of exam bar codes identifying a plurality of unique body parts of a patient and a plurality of x-ray exposure conditions;

hand-held bar code scanner having a user input, a memory, a digital controller, and a display, for scanning the patient bar code, the storage phosphor bar code and a bar code from at least one of said fields of bar codes on said exam bar code chart;

a required fields control card having bar codes representing required bar code fields required to be scanned into the bar code scanner by a bar code scanner user before the scanner allows a record to be completed, wherein said required bar code fields includes a patient bar code, a storage phosphor bar code, and an exam bar code from said x-ray exam bar code chart; and a default values control card having bar codes representing default values bar code scanner commands and bar codes representing default values for exam characteristics which need not be scanned at the time of an x-ray exam.

2. The system of claim 1 wherein said patient identifying bar code is an encoded bar code or an unencoded patient bar code, wherein said encoded patient bar code can be directly scanned into said bar code scanner, and wherein said bar code scanner must first be conditioned before it can read in said unencoded patient bar code.

3. A patient identification and x-ray exam data collection bar code system, comprising:

a patient bar code located with a patient for identifying a patient;

a storage phosphor for storing an x-ray image of a patient, said storage phosphor having a storage phosphor bar code for identifying the storage phosphor;

x-ray exam bar code chart locatable with an x-ray source for identifying x-ray examination characteristics of said x-ray image stored in said storage phosphor, wherein said exam bar code chart includes fields of exam bar codes identifying a plurality of unique body parts of a patient and a plurality of x-ray exposure conditions;

hand-held bar code scanner having a user input, a memory, a digital controller, and a display, for scanning the patient bar code, the storage phosphor bar code and a bar code from at least one of said fields of bar codes on said exam bar code chart;

a required fields control card having bar codes representing required bar code fields required to be scanned into the bar code scanner by a bar code scanner user before the scanner allows a record to be completed, wherein said required bar code fields includes a patient bar code, a storage phosphor bar code, and an exam bar code from said x-ray exam bar code chart; and a technologist bar code for identifying the technologist performing said x-ray exam, wherein said technologist bar code can take the form of an encoded bar code or an unencoded bar code, wherein said encoded technologist bar code can be directly scanned into said bar code scanner, and wherein said bar code scanner must first be conditioned before it can read in said unencoded technologist bar code.

\* \* \* \* \*